United States Patent [19]
Charych et al.

[11] Patent Number: 6,001,556
[45] Date of Patent: Dec. 14, 1999

[54] POLYMERIC ASSAY FILM FOR DIRECT COLORIMETRIC DETECTION

[75] Inventors: Deborah Charych, Albany; Jon Nagy, Rodeo; Wayne Spevak, Albany, all of Calif.

[73] Assignee: The Regents of the University of California, Calif.

[21] Appl. No.: 08/592,724

[22] Filed: Jan. 26, 1996

Related U.S. Application Data

[63] Continuation of application No. 08/159,927, Nov. 30, 1993, abandoned, which is a continuation-in-part of application No. 07/982,189, Nov. 25, 1992, abandoned, and application No. 07/976,697, Nov. 13, 1992, abandoned.

[51] Int. Cl.$^6$ ...................................................... C12Q 1/70
[52] U.S. Cl. .............................. 435/5; 435/518; 435/531; 435/528; 435/7.1; 435/164; 435/4; 435/6; 422/55; 422/57; 422/58; 422/82.05; 422/82.09; 427/2; 428/441; 428/442
[58] Field of Search .................................... 435/518, 531, 435/528, 7.1, 164, 4, 5, 6; 422/55, 57, 58, 82.05, 82.09; 427/2; 428/441, 462

[56] References Cited

U.S. PATENT DOCUMENTS

| | | |
|---|---|---|
| 4,859,538 | 8/1989 | Ribi . |
| 5,268,305 | 12/1993 | Ribi et al. . |
| 5,415,999 | 5/1995 | Saul et al. . |
| 5,427,915 | 6/1995 | Ribi et al. . |
| 5,480,582 | 1/1996 | Pope . |
| 5,491,097 | 2/1996 | Ribi et al. . |
| 5,521,101 | 5/1996 | Saini et al. . |
| 5,571,568 | 11/1996 | Ribi et al. . |
| 5,618,735 | 4/1997 | Saul et al. . |
| 5,622,872 | 4/1997 | Ribi . |

OTHER PUBLICATIONS

Charych et al Mat. Res. Symp. Proc. vol. 292 (1993) pp. 153–161.
Arab et al Glycoconjugate Journal (1996) 13: 159–166.
Pons et al Biochimica et Biophysica Acta 693 (1982) 461–465.
Yuan et al Solid State Communications vol. 80 No. 7 (1991) 493–495.
Charych et al Science vol. 261 (1993) 585–588.
Arisawa et al., "Quantitative characterization of enzymes adsorbed on to Langmuir–Blodgett films and the application to a urea sensor," *Thin Solid Films* 210:443–445 (1992).
Beswick and Pitt, "Optical Detection of Toxic Gases Using Fluorescent Porphyrin Langmuir–Blodgett Films" *J. Colloid Interface Sci.* 124:146–155 (1988).
Chance et al., "Thermal effects on the optical properties of single crystals and solution–cast films of urethane substituted polydiacetylenes," *J. Chem. Phys.* 71:206–211 (1979).
Day et al., *Journal of Polymer Science, Letters to the Editor* 16:205 (1978); reference unavailable—will be provided at a later date.
Ehlen et al., "Organic Clathrate–Forming Compounds as Highly Selective Sensor Coatings for the Gravimetric Detection of Solvent Vapors," *Angew. Chem. Int. Ed. Engl.* 32:110–112 (1993).
Furuki and Pu, "Hybrid gas detector of squarylium dye Langmuir–Blodgett film deposited on a quartz oscillator," *Thin Solid Films* 210: 471–473 [1992].
Kaneko et al., "Absorption properties and structure changes caused by pre–annealing in polydiacetylene Langmuir–Blodgett films," *Thin Solid Films* 210/211:548–550 (1992).
Mino et al., "Photoreactivity of 10,12–Pentacosadiynoic Acid Monolayers and Color Transitions of the Polymerized Monolayers on an Aqueous Subphase," *Langmuir* 8:594–598 (1992).
Miyasaka et al., "Amperometric Glucose Sensor with Glucose Oxidase Immobilized on $SnO_2$ Electrode via a Monolayer of a Photoreactive Nitrophenylazide Derivative," *Chem. Lett.,* p. 627–630 (1990).
Novotny et al., "Tribology of Langmuir–Blodgett Layers," *Langmuir* 5:485–489 (1989).
Okahata et al., "Preparations of Langmuir–Blodgett Films of Enzyme–Lipid Complexes: A Glucose Sensor Membrane," *Thin Solid Films* 180:65–72 (1989).
Roberts (ed.) Langmuir–Blodgett Films, Wiley, New York (1966).
Shibata, "Reversible Colour Phase Transitions and Annealing Properties of Langmuir–Blodgett Polydiacetylene Films" *Thin Solid Films* 179:433–437 (1989).
Spevak et al., "Polymerized Liposomes Containing C–Glycosides of Sialic Acid: Potent Inhibitors of Influenza Virus in Vitro Infectivity," *J. Am. Chem. Soc.* 115: 1146–1147 [1993].
Swalen et al., "Molecular Monolayers and Films," *Langmuir* 3:932–950 (1987).
Tieke, "Langmuir–Blodgett Membranes for Separation and Sensing," *Adv. Mat.* 3:532–541 (1991).
Whitesides et al., "Wet Chemical Approaches to the Characterization of Organic Surfaces: Self–Assembled Monolayers, Wetting, and the Physical–Organic Chemistry of the Solid–Liquid Interface," *Langmuir* 6:87–96 (1990).
Berman et al., "Total Alignment of Calcite at Acidic Polydiacetylene Films: Cooperativity at the Organic–Inorganic Interface," *Science* 269:515–518 (1995).
Charych et. al., "A 'litmus test' for molecular recognition using artificial membranes," *Curr. Biol.* 3:113–120 (1996).

(List continued on next page.)

*Primary Examiner*—Anthony C. Caputa
*Assistant Examiner*—Heather A. Bakalyar
*Attorney, Agent, or Firm*—Medlen & Carroll, LLP

[57] ABSTRACT

A lipid bilayer with affinity to an analyte, which directly signals binding by a changes in the light absorption spectra. This novel assay means and method has special applications in the drug development and medical testing fields. Using a spectrometer, the system is easily automated, and a multiple well embodiment allows inexpensive screening and sequential testing. This invention also has applications in industry for feedstock and effluent monitoring.

31 Claims, 6 Drawing Sheets

OTHER PUBLICATIONS

Charych et al., "Specific Interaction of Influenza Virus with Organized Assemblies of Polydiacetylenes," *Mat. Res. Soc. Symp. Proc.* 282:153–161 (1993).

Dagani, "Lipids and Minerals Form Novel Composite Microstructures," *Chem. & Eng. News,* 19–20 (1993).

Kessel and Granick, "Formation and Characterization of a Highly Ordered and Well–Anchored Alkylsilane Monolyaer on Mica by Self–Assembly," *Langmuir* 7: 532–538 (1991).

Kingery–Wood et al., "The Agglutination of Erythrocytes by Influenza Virus is Strongly Inhibited by Liposomes Incorporating an Analog of Sialyl Gangliosides," *J. Am. Chem. Soc.* 114:7303–7305 (1992).

Leung et al. ,"Imaging of polydiacetylene on graphite by scanning tunneling microscopy," *J. Appl. Phys.* 69(4):2044–2047 (1991).

Lio et al., "Atomic force microscope study of chromatic transitions in polydiacetylene thin films," *J. Vac. Sci. Technol.* 14(2):1481–1486 (1996).

Miyasaka et al., "Oriented Polypeptide Monolayers by Rapid Spontaneous Condensation of Amphiphilic Amino Acid Esters," *The Solid Films* 210/211:393–396 (1992).

Ott et al., "Liposomes and influenza viruses as an in vitro model for membrane interactions II. Influence of vesicle size and preparation methods," *Eur. J. Pharm. Sci.* 6:333–341 (1994).

Perez et al., "Toward Inorganic Monolayers Inserted in a Langmuir–Blodgett Matrix," *Thin Solid Films* 210/211:410–411 (1992).

Pons et al., "The Optical Activity and Circular Dichroic Spectra of Diacetylenic Phospholipid Polymers," *Biochim. Biophys. Acta* 693:461–465 (1982).

Rieke et al., "Spatially Resolved Mineral Deposition on Patterned Self–Assembled Monolayers," *Langmuir* 10:619–622 (1994).

Reichert et al., "Polydiacetylene Liposomes Functionalized with Sialic Acid and Colorimetrically Detect Influenza Virus," *J. Am. Chem. Soc.* 117:829–830 (1995).

Spevak, "The Presentation of Biological Ligands on the Surface of Polymerized Monolayers and Liposomes," Ph.D. Dissertation, University of California at Berkeley (1993).

Tanev and Pinnavaia, "Biomimetic Templating of Porous Lamellar Silicas by Vesicular Surfactant Assemblies," *Science* 271:1267–1269 (1996).

Yamanaka et al., "Solid Phase Immobilization of Optically Responsive Liposomes in Sol–gel Materials for Chemical and Biological Sensing," *Langmuir* 13:5049–5053 (1997).

POLYMERIC ASSAY FILM FOR DIRECT COLORIMETRIC DETECTION

This is a continuation of application Ser. No. 08/159,927 filed on Nov. 30, 1993, now abandoned, which is a Continuation In Part of prior-file U.S. patent application Ser. No. 07/982,189 filed Nov. 25, 1992, now abandoned and U.S. patent application Ser. No. 07/976,697 filed Nov. 13, 1992, now abandoned.

This invention was made with Government support under Contract No. DE-AC03-76SF00098 between the U.S. Department of Energy and the University of California for the operation of Lawrence Berkeley Laboratory. The Government has certain rights in this invention.

BACKGROUND OF THE INVENTION

The present invention relates to a method for direct detection of analytes using observable spectral changes in monomolecular films which occur upon the analytes selective binding to the film.

Analytical Chemistry

Analytical chemistry techniques have been used for many years to determine such medical parameters as hematocrit levels. While useful in their own right, analytical chemistry methods are of limited or no practical applicability to many biological parameters in which assessment would be valuable. Unless expensive and cumbersome gas chromatography methods are used, large quantities of analytes are generally required to accomplish such methods. Often, quantitative results are limited or not available. However, such techniques have been used for such basic chemical tests as creatinine assays.

Microbiological and Pathology Methods

Another approach to medical-biological systems analysis has been direct microscopic observation using various cell-staining and classic pathology techniques. Augmenting these capabilities have been well developed microbiological techniques, such as culturing, colony characterization, and observation of metabolic and nutrient limitations. Most of medical science has been developed using this basic arsenal of analytic techniques.

While culturing and direct tissue observation techniques have served as the bulwark of medical detection processes for many years, they have considerable limitations. Pathological analysis of patient tissues to determine the development of a disease state and the identification of the causative pathogen generally requires an invasive procedure. On the other hand, culturing the pathogen from various body fluid or other samples is time consuming and expensive.

Immunoassays

A breakthrough in medicine occurred with the development of immunoassay techniques. In these methods, an antibody is developed which will specifically bind to a target of interest. While costly in both their development and production, antibodies from animals allowed a very accurate analysis of a number of analytes which had previously been virtually unassessable in both research and particularly clinical situations.

An important technical advancement in immunoassay was the development of monoclonal antibodies. Instead of subjecting an animal to an analyte and harvesting its whole range of antibodies, in this techniques a single spleen cell of a sensitized animal is rendered immortal and multiplied many times. The resulting cell line is then cultured to produce a very specific and pure antibody product.

Because the antibody itself is a small molecule, it must be labeled in some way so that the binding event can be detected. This can be done with a dye, flourescent, radioactive or other label. Conversely, if binding inhibition occurs between a known amount of introduced, labeled analyte and the material to be analyzed, the diminution of the signal will indicate the presence of test analyte. If the agglutination of the antibody particles is of sufficient volume and density, the formation of a precipitant can also serve to signal the presence of an analyte.

In recent years, the research and medical communities have come to rely heavily on immunoassay techniques to detect and quantify biological materials. While successful in many respects, the indirect nature of immunoassay methods as well as their dependence on antibody materials, results in a variety of complications, problems, and assay limitations. Briefly, the development and production of antibodies remains expensive, and these molecules are sensitive to environmental changes. Also, only those materials to which antibodies can be produce can be detected by these systems.

Immobilization of Assay Components

Many types of analytical chemistry techniques can be optimized and their implementation expedited by the immobilization of one or more of the components of a reaction. For instance, if the material to be tested is present in only a small quantity in a test sample, the analyte may be at so small a concentration that it is beyond the detection capabilities of a particular assay system.

Many immobilizing materials are available. These materials have been used extensively in analytical chemistry procedures for such purposes as the concentration materials. Sephadex columns are very commonly used for such purposes. Except for their specific binding properties, it is preferred that immobilization materials are relatively inert so that they themselves do not interact in the test reaction or otherwise interfere with the assay. Another important quality for immobilization materials is that they be regular in their structure, so as to provide predictability in the testing situation.

Classically, immobilization has been accomplished on columns, liposomes or other surfaces. The use of such materials provides many advantages for an assay system. For instance, these materials allow easy segregation of reactants from the surrounding test washes. Bi-lipid layer surfaces on support structures, as is described below, are also serving an immobilizing role in analytical systems.

In a typical immobilization scheme, the analyte is concentrated by adhesion to a column for which it has affinity. The testing can then take place on a limited area surface, rather than in the defused three-dimensional array of the original sample fluid. The reaction of the results are then concentrated in a smaller area, and are more likely to reach the level of detectability. A number of iterations of this technique are equally applicable to assay systems. These include concentrating the bound reactants to achieve an intensified signal, binding the signal producer and reacting the analyte on that surface, etc.

Immobilization techniques have proven very useful in the case of immunoassay approaches. Some of the difficulties with immunoassays lie in the submicroscopic nature of these materials. In a free-floating system, it is difficult to separate various parts of a sample which can obscure results, and to assure the maintenance of critical materials. For instance, there may only be a small amount of analyte in a sample, and the antibody can be very expensive, so that pure agglutination procedures will not accomplish a practical assay.

In response to these limitations, the research community has developed means of "immobilizing" the various components of an assay, both to concentrate analyte, and to localize a binding event. Basically, one component of the test is "tacked down" to a surface, and anything which subsequently binds to that component is likewise immobilized. This approach allows many advantages in using immunoassay techniques to their full potential.

An example of the use of immobilization in immunoassay techniques is where a test sample is washed across a surface to which it binds. An antibody is then washed across this treated surface, allowing specific immunogenic binding to occur. The antibody may have been pre-treated with a tag, in which case a color change, fluorescences or other such label is observed in a small, limited area. This approach provides maximum efficiency by limiting the amounts of both analyte and test materials required.

Bilayer Films as Immobilizing Supports

Bilayer films on surfaces have been used to provide the qualities of relatively expensive film materials to low cost support bases. Chemical modification of surfaces by organic monomolecular films has recently been used in an effort to develop such new materials. The ultrathin film coatings which can be achieved by these new approaches can effectively alter the surface properties of the original underlying material.

Because of these motivations, the techniques of molecular self-assembly, such as that described by Swalen et al., (*Langmuir*, Vol. 3, page 932, 1987) as well as Langmuir-Blodgett (LB) deposition (Roberts, Ed. *Langmuir-Blodgett Films*, Wiley, New York, 1966) are being used for coating surfaces with a well-defined, quasi two-dimensional array of molecules. The initial use for this new advancement was for materials science applications such as wetting (Whitesides, et al., *Langmuir*, Vol. 6, p. 87, 1990) and friction (Novotny et al., *Langmuir* Vol. 5, p. 485, 1989).

These bilayer films are also being used as immobilizing supports for analytic reactions. Bio-sensors based on LB films can detect molecules of diagnostic significance such as glucose (Okahata, et al., *Thin Solid Films*, Vol. 180, p. 65, 1989) and urea (Arisawa, et al., *Thin Solid Films*, Vol. 210, p. 443, 1992). In these cases, classic analytical chemistry systems are immobilized on the films in order to improve the readout of the test results and otherwise simplify and improve the detection capabilities of the test procedure.

The detection of receptor-ligand interaction is generally accomplished by indirect assays such as the enzyme-linked immunosorbent assay. Although biotechnological functionalized films have led to elegant examples of molecular recognition at an interface, the problem of transducing the molecule recognition event into a measurable signal has remained a difficulty until the advent of the subject invention.

In the case of biosensor devices, detection is generally carried out by coupling the LB films to a secondary device such as an optical fiber (Beswick, *Journal Colloid Interface Science*, Vol. 124, p. 146, 1988), quartz oscillator (Furuki et al., *Thin Solid Films*, Vol. 210, p. 471, 1992), or electrode surfaces (Miyasaka, et al., *Chemical Letters*, p.627, 1990).

Some of the analytes bound to these films provide for fluorescent label, where the fluorescence or its quenched state indicate the occurrence of a binding event (Beswick, *Journal Colloid Interface Science*, Vol. 124, p. 146, 1988). In some cases, these detection materials have been embedded in the surface of the supporting bi-lipid layer (Tieke, *Advanced Materials*, Vol. 3, p. 532, 1991).

Polydiacetylene films are known to change color from blue to red with an increase in temperature or changes in pH due to conformational changes in the conjugated backbone (Mino, et al., *Langmuir*, Vol. 8, p. 594, 1992; Chance, et al., *Journal of Chemistry and Physics*, Vol. 71, p. 206, 1979; Shibutag, *Thin Solid Films*, Vol. 179, p. 433, 1989; Kaneko, et al., *Thin Solid Films*, Vol. 210, p. 548, 1992). While it has been a goal of the research community to exploit this characteristic in the detection of binding events, researchers have yet to develop a method using this phenomenon in practical applications.

It would be highly desirable if the direct detection method of analytical chemistry techniques could be achieved with very small and biological molecules present in minute amounts in the analytic fluid, as this would represent a revolution in the bio-medical analytic arts. It would be ideal if the technology of monomolecular film supports could be developed in a unique way so that the binding event causes a change in the support material that could be directly detected.

GENERAL DESCRIPTION OF THE INVENTION

The present invention allows, for the first time, direct detection of small molecules, such as pathogens and drugs, using observable spectral changes in monomolecular films. The present invention represents an entirely new approach to the direct detection of a material using color changes in a monomolecular film which occurs when specifically bound to the target molecule.

It is an object of the present invention to assay the presence of biomolecules by directly detecting the binding event when the analyte specifically binds to a polymer bilayer.

It is a further object of the present invention to provide for the direct detection of viruses, bacteria, parasites, and other pathogens, and drugs, biomedical materials, industrial materials, hormone, cell wall fragments, enzymes and their interactions, as well as other biologically relevant materials such as blood components, disease indicators, cell components, antibodies, lectins, and genetic material.

Detected viruses include influenza, cold, rubella, chicken pox, hepatitis A, hepatitis B, herpes simplex, polio, small pox, human immuno-deficiency virus, vaccinia, rabies, Epstein Barr, reovirus, rhinovirus, and mutations, strains, and ligand recognizable parts thereof. Detected bacteria include *E. coli*, M tuberculosis, salmonella, Streptococcus, and mutations, strains and degraded pates thereof. Detected parasites and other pathogens include those responsible for malaria, sleeping sickness, river blindness, and toxoplasmosis.

It is another object of the present invention to provide for the development and improvement of drugs by observing competitive inhibition of natural binding events between all surfaces or binding sites and their natural bioactive ligand.

It is yet another object of the invention to detect the presence of biomolecules by spectral changes (color changes visible to naked eye or with calorimeter) in the inventive lipid bilayer which occur as a result of the specific binding of the biomolecules to the bilayer.

It is an additional object of the present invention to provide a simple to use, inexpensive test kit whose reliability is relativity stable in a wide range of environmental conditions, and when the analyte is mixed with a number of other materials.

The present inventive assay means and method provide for the direct calorimetric detection of a receptor-ligand interaction using a novel polymeric thin film construct. Using the inventive method of producing these original thin films, a ligand or its derivative are rendered polymeric by polymeric linking of the ligands through a linking arm to a polymerized thin bi-layer film. The presence of an analyte which binds to the ligands is observed through changes in the spectral characteristics of the polymeric film. The polymer-ligand assembly thus encompasses a molecular recognition site and a detection site, all contained within a single molecular assembly.

In one embodiment of the invention, a thermo-chromatic polydiacetylene bilayer is assembled on a support, and then used for the detection procedure. The polydiacetylene layer is functionalized with a receptor specific ligand for the target molecule which is to be detected. Both qualitative and quantitative findings as to the presence of the target material can be obtained using various embodiments of the subject invention.

Advantages of the Invention

Analytical Chemistry Techniques

Analytical chemistry techniques have limited applicability to many biological systems assays. Unless expensive and cumbersome gas chromatography methods are used, large quantities of analyte are required. Often, quantitative results from such methods are limited or not available. However, such techniques have been used for such tests as hematocrit analysis, and creatinine assays.

Analytical chemistry methods are virtually unavailable for most biological molecules due to the destruction of the analytes characteristics during preparation and analysis steps, and the typically small amount of the analyte present in the test sample. For these reasons, the advent of immunoassay techniques were revolutionary in the biological sciences.

Immunoassays

Many small biological molecules are notoriously difficult to assay in a direct manner due to the severe limitation of environmental ranges which they can tolerate without losing their specific characteristics. For these among other reasons, immunoassays have been heavily relied upon to assay these classes of materials. While successful in many respects, the indirect nature of immunoassay methods results in a variety of interferences, complications, problems, and assay limitations.

The requirement that an antibody be developed and produced for each possible target limits the efficacy of immunoassay methods in such applications as designer drug development and screening. Ironically, while allowing testing within a portion of biological environmental ranges, the large glycoproteinaceous antibody are often highly sensitive to degradation outside of a small testing parameter environmental range. Thus, the susceptibilities of antibodies too rigorously limit the environmental testing range available in these assay systems.

A subtle disadvantage to immunoassay systems occurs in rapidly evolving pathogens such as the influenza virus. In such organisms, especially in the case of viruses, the external coat which is available for immune reactions has become constantly shifting in its antibody recognition elements. Thus, despite a full blown immunity response to an influenza strain, within months an individual can again develop flu, but from a pathogen with an external coat so modified that it is immunologically unrecognizable by the victims memory cells. This is the reason individuals can develop flu year after year.

In contrast to assays requiring binding to immunoglobulins, in one embodiment of the present invention, the host attachment site on the pathogen is exploited for recognition function. This site, generally in an immunologically inaccessible valley on the pathogen surface, is highly genetically conserved over time. The minimal variability of this site is necessary for the pathogen to maintain its infectivity. As a result, a single assay system of the present invention will provide effective assays for a panoply of influenza strains, many of which may be very newly evolved.

There are many advantages to the genetically conserved host recognition site being targeted by the embodiment of the present invention. A determination of a patient's exposure to the flu will be definitive, and not limited to a particular strain. This advantage of the present invention also avoids the need for a large number of immunological tests, as the clinician can rely on a single assay. Additionally, even newly evolved, uncharacterized flu strains can be identified, further avoiding false negative tests.

An analogous limitation of immunoassays occurs in well established pathogens such as malaria parasites. In these organisms, phases of the life cycle which would allow for an immune response have over time been so limited as to avoid the immune response, or have been made to occur within host cells so as to avoid an antibody reaction.

The present invention exploits the genetically conservative host binding site to identify the pathogen. Even in comparatively large parasites, the host binding site tends to be held constant over time throughout the generations of pathogens. Additionally, parasites are usually present in the body in a large number of diverse life stages. In well established parasites, the immune accessible sites often vary considerably from stage to stage, the advantage being that the host organism is unable to mount a immunological response with sufficient rapidity to avoid the entrenchment of the parasite.

General Advantages of the Invention

The subject invention represents a dramatic advancement over both prior art direct chemical and immunoassay systems, achieving advantages which, prior to the present invention, where available exclusively in only one or the other of these analytic art methods. Much as the advent of immunoassay techniques revolutionized medical and research analytical capacities, the subject invention represents a critical advance in the analytical arts.

The present invention allows the advantages of both immunoassay and chemical analysis in a single system. The present invention enjoys the direct assay advantages of analytical chemistry methods, with many of the advantages inherent in such systems. The inventive assay technique also has a substantial environmental range of testing beyond that of immunoassays. This allows the accommodation of various analytes in their most advantageous environmental parameters. Additionally, the present invention allows rigorous, direct analysis to occur even in very narrow environmental ranges, previously unavailable with analytical chemistry techniques. The speed and simplicity of the color change indicator of the subject invention are its hallmark advantages.

Target Materials

One of the unique advantages of the subject invention is the wide range of target materials, binding events, and biochemical reactions amenable to analysis using the inventive techniques. Many of these materials previously could not be detected using a straightforward, practical assay. The present invention allows many advantages of immunoassay systems, without the complications of immunoglobulin generation or indirect analysis.

In general, the present invention requires no pre-analysis purification step. This feature of the subject invention is due to the high specificity of the ligands incorporated into the detecting film. Additionally, the inventive direct assay system avoids the expense, complications, and increased inaccuracies inherent in the indirect systems currently available.

Sensitive Analytes-Gentle Testing Conditions

The inventive polymeric thin film construct can employ ligands and analytes which are stable or enjoy appropriate binding characteristics only within a limited in vitro or environmental range of conditions. Within the limitations of in vitro range conditions, the present invention is useful in that stringent limitations even within this narrow range of conditions can be met. This allows, for instance, three dimensional conformations of sensitive biochemicals and biomolecules to be maintained throughout the testing procedure.

The present invention functions well even in carefully limited conditions. Thus, conditions such as pH, saline, and temperature can be carefully controlled by feedback controls, titration and other techniques without interfering with the accuracy or sensitivity of the analysis.

Because of this wide experimental range advantage of the present invention, intact cells or sensitive subcellular inclusions can be assayed without disturbing their structural integrity. Subtle cellular development stages can be monitored, such as the various stages of malaria infection. Additionally, the association between various factors can be tested or monitored even during the interaction process using the method of the subject invention.

Weak Binding Analytes-Multivalency

The multivalent feature of the polymer-linked ligands of the subject invention provide a heightened binding capacity in the case of naturally multivalent analytes. Multivalency can also be provided for limited valency analytes prior to the test procedure to imbue them with this advantage of the subject invention. The inventive exploitation of multivalency allows a specific but weak interaction to be amplified many fold.

A structural linker of sufficient length and conformability aids in allowing binding of multiple sites on the analyte even when they are conformationally separated on a curved surface. As a result of these special features, the present invention can detect many ligands previously unsuitable for assay evaluation.

The main criteria for effective indication of the presence of analyte is that the surface of the indicating bilayer be sufficiently perturbed to produce the requisite spectral change. Binding the analyte to an immobilizing particle well serves this purpose, as it concentrates the analyte in a small area, and further provides a three-dimensional aspect over a relatively large area to even a small analyte.

A large variety of ligands can be employed in the subject invention, allowing great flexibility in detecting a multivalent test target. Ligand selection can be based on the most advantageous binding and steric characteristics, rather than compromising these factors to accommodate the test system. Thus, the most advantageous ligand can be selected based on such factors as hydrophobicity and hydrophilicity, size, position of binding site, and conflicting affinities. Ligands which can be employed in the subject invention can include carbohydrates, peptides, nucleotides, heterocyclic compounds, and other organic molecules.

Challenging Analytes

The rigor and outstanding advantages of the inventive assay system allows the detection and quantitative evaluation of materials which have been previously unachievable because of the limitations of the prior art methods. The present inventors have already exploited the unique advantages of the present inventive means and method to achieve a unique assay method which accurately detect malaria parasitic infection (see Example 5 below). Development of an effective assay for malaria in transient stages has hitherto proven an intractable challenge for either the immunological assay or analytical chemical art methods.

The inventive construct and method can assay very small biological or other molecules for which antibodies can not be developed. These target materials can include organic solvents or pollutants present at extremely low levels. There are special opportunities made available by the advances achieved by the subject inventors for drug screening in both forensic and clinical applications. Inhibition techniques applied to the subject invention can allow the testings of materials which are of a tiny size or have a small number or single valiancy.

While applicants are not bound there by, it is hypothesized by the inventors that the unexpected spectral signal achieved by the present invention is due to a physical perturbation of the bilayer which occurs as a result of the binding event. It is the case that multivalent materials, such as viruses and cell membrane fragments, can be very easily detected using the subject inventive method. Thus, multivalent materials generally elicit a particularly strong response in the subject system. This may be the case because of conformational changes introduced into the bi-lipid layer as a result of binding causing physical reconfiguration of structure.

If applicants' theory holds true, pre-binding of smaller, single valent analyte materials to a carrier may prove advantageous to increasing the efficacy of the subject invention in those cases.

For instance, the analyte could be bound to a polymer or the surface of a liposome. This would concentrate the binding event on the inventive bilipid surface to specific points, increasing the spectral modification at each point of contact. Additionally, the curved surface of the liposome to which the analyte is attached will likely serve to tug the peripheral bound analytes away from the bilipid surface and force analytes centrally located on the liposome into the bilipid surface. This pre-binding step then can result in increased torsion, perturbation and signal generation on the bilayer surface.

Signal Observation

Various spectral changes to the bi-layer can be used to detect the presence or absence of the target material. Means of amplifying the spectral signal well known in the art, such as scintillators, can also be employed when low levels of analyte are present. Because of the empirical nature of the signal, there are many opportunities for automating the read out of the present inventive assay system.

In one particular embodiment of the present invention, a blue-red color shift can be observed simply by visual observation by the testing technician. Because of the simplicity of the observation, this function can easily be accomplished by an untrained observer such as an at-home user. Alternatively, spectral test equipment well known in the art can be employed to determine a change in spectral qualities beyond the limits of simple visual observation, including optical density to a particular illuminating light wavelength.

Spectral changes outside the human visual range can be employed effectively in the subject invention by use of various spectral analyzers, such as light meters, or through technician observation of the surface using various translating devices, such as infrared and ultraviolet detectors.

In one embodiment of the present invention, the bilayer is composed of a self-assembled monolayer of octadecyltrichlorosilane and a Langmuir-Blodgett monolayer of polydiacetylene. The polydiacetylene layer in this case is functionalized with an analog of sialic acid, such as that described in parent case U.S. application Ser. No. 976,697, filed Nov. 13, 1992. Sialic acid is the receptor-specific ligand for the influenza virus hemagglutinin, as well as for other pathogens. The sialic acid ligand serves as a molecular recognition element.

The conjugated polymer backbone of the polymerized bilayer assembly signals binding at the surface of the film by a chromatic transition. The color or other spectral transition can be readily visible to the naked eye as a blue to red color change and can be quantified by visible absorption spectroscopy. This particular embodiment of the present invention is described in more detail in Example 1 below.

Applications

The subject invention enjoys broad applications to the detection of a very wide variety of analytes. These include small biomolecules, the observation of binding and other chemical events, and the detection of trace amounts of many materials.

Because of the very broad applicability, important classes of analytes are detectable by the present invention which have previously proven difficult or impossible to detect by prior art methods. Many viruses, bacteria and proteins related to them or their infection of a patient can be detected. These include such pathogens as influenza, HIV, and malaria among others. Direct colorimetric detection by the inventive polydiacetylene films offers new possibilities of diagnostic application and screening for new drug candidates or binding ligands.

Designer Drug Development

An extremely important use of the present invention is for designer drug development and screening. Currently, radio-labeled materials are typically used to assess competitive inhibition of drug receptor molecules. However, this is a time-consuming process and requires access to and handling of radio-labeled materials. Even other techniques, such as fluorescence quenching, are limited in that each test is self-contained, and so a large screening effort is prohibitively time consuming and expensive.

In this particular application of the subject invention, various iterations of a drug can be quickly screened for interference with infective binding by a pathogen. Table 1 provides a number of examples of the host receptor molecules which provide the site of pathogen attachment required for infectivity. All of these examples, along with many others, can be exploited by the subject invention for drug development and optimization. Multiple wells on a single bilayer sheet allow many subtle iterations of a candidate drug to be tested, such as various levels of pH titering. The current chilling effect on drug research of expensive, individual testing for each sample would be eliminated.

The availability of high-volume inexpensive screening will dramatically increase the speed of drug development, similarly to the effect the development of new mass screening techniques had in molecular biology. Naturally occurring transmembrane receptors (TMR) can be reconstituted into a lipid bilayer where the lipid layer is constructed from the polymerizable monomers. This is particularly applicable to the inventive compounds that have the two triple bonds in the chain. Once the receptor is incorporated into the lipid, the lipid can be irradiated and polymerized to 'lock' the TMR in place. Binding of small molecules to the binding site in the TMR produces a conformational change in the TMR which affects the lipids and causes a color change.

A wide variety of TMR's have been isolated. TMR's including hormone, neurotransmitter, and other physiological regulating receptors, are particularly useful in the improvement and development of drugs using the present invention. The use of naturally occurring TMR's (described below) in the subject invention has particular applications to drug screening. That application of the subject invention has immediate pertinence in the development of new drugs who function by binding to membrane bound receptors. These receptors can be isolated, and include the dopamine receptor, among a number of others. By example, the dopamine receptor binds the natural compound dopamine. In order to employ the subject invention to search for new compounds that behave like dopamine (i.e. bind to the dopamine receptor). The schemes set out below on Example 2 show the embodiment of the present inventive films and their applications.

Because of the ease of screening available using the subject invention, many small changes can be made in the candidate drug structure and analyzed immediately, providing great speed and flexibility in drug development and optimization. By noting the area of modification which provides the greatest changes in effectiveness, the critical structures of the drug can be rapidly identified. This allows a critical focusing of the drug modification effort which will greatly increase the speed of drug development.

Even more basic research into drug interactions, optimization, and new drug development is also made practical by the present invention. Existing drugs can be analyzed to determine which structures are of the greatest importance in their therapeutic effect. These structures can then be optimized, and even transposed on to a more biologically acceptable, smaller, or less expensive non-active structure. Such qualities as the ability to traverse the blood-brain barrier can be conferred.

If two different drugs are available for the treatment of disease, their structure can be analyzed as to activity using the technology of the subject invention. Then, their active sites can be incorporated into a single drug. Additionally, attendant structures which optimize activity can be appropriately situated on the new hybrid drug. Any interference in activity can be determined and ameliorated or eliminated prior to expensive and lengthy animal or human trials.

Medical Assay Applications

Another extremely important application for the subject inventive means and method is the inexpensive, accurate assaying of infective states and other medical conditions. For instance, antibody levels to a specific pathogen can be easily and inexpensively monitored through competitive inhibition of a set amount of pathogenic material placed in the analytic solution. Additionally, certain antibodies can be detected through their direct and specific binding to the inventive membrane.

A large variety of biologically related materials are advantageously susceptible both to quantitative and qualitative analysis using the subject invention. Infection by various pathogens can be tested for long before clinical manifestations are observed. This is a particularly critical advantage with patients who have depressed immunity, such as in newborns, chemotherapy patients, donor organ recipients, and AIDS victims.

Fertility and Prenatal Applications

In testing for pregnancy, Human Chorionic Growth hormone is assayed using the present invention. A rise in luteinizing hormone will herald the onset of ovulation for both the achievement of pregnancy and for use in natural birth control methods.

Because of the simplicity of readout, the subject invention is highly suited for the home market. Also, multiple testing at a low cost is a real advantage. It is necessitated in natural birth control methods, and is generally required in assessing fertility to optimize the chances of achieving pregnancy.

The inexpensive multiple testing capacity of the present invention made possible through multiple wells on a single bilayer sheet provides an excellent incentive for extremely early detection of pregnancy. Detecting pregnancy prior to a missed period is important in avoiding exposure to harmful factors which are of such criticality in final outcome in the first few days of pregnancy.

It is of prime importance when a pregnant woman may have been exposed to a disease that will have late or no clinical manifestation for the mother, but could severely damage the developing fetus she carries. These diseases can include rubella, toxoplasmosis, and other pathogens. The present invention allows for simple and inexpensive screen for such diseases.

Diabetes

Another important application for the present invention is the monitoring of patients with chronic illnesses such as diabetes. For instance, insulin blood levels can now be regularly monitored at home using the subject invention. This will allow diabetics to tailor their insulin administration to more accurately follow their bodies general cycles of insulin requirements. It will also allow them to quickly differentiate whether early symptoms are due to transients illness such as flu or to undue variations in insulin levels.

Cholesterol

The present invention also allows for the production of a simple, at-home test for cholesterol levels. In the higher end product of these kits, full cholesterol profiles will be provided. This allows patients to determine their cholesterol levels in the privacy of their own home, encouraging the more reticent to accomplish the test and be appraised of this often critical information.

For patients with known hypercholesterolnemea, the present invention represents an ideal means to closely monitor the palliative effects of treatment efforts. The multiple well test kit made possible and practical by the present invention is particularly useful for weekly or even daily monitoring of these levels. For instance, in some individuals, diet modification has a dramatic effect on ameliorating high cholesterol levels. In such individuals, straying from the diet will produce an increase in levels. The immediate feedback of the subject invention thus provides a strong incentive for long term diet compliance.

Drug Monitoring

The monitoring of drugs and drug levels is a fertile area of application for the present invention. Patients typically display a wide range of metabolic levels and liver activity. This is particularly the case for those in a hospital situation. Because blood drug levels can not be easily determined, the clinician is often forced to under-medicate a patient who could benefit from higher levels of administration. Unfortunately, the doctor must error on the side of caution to avoid the possibility of toxic levels being reached. The present invention allows a more accurate titering of drug administration, allowing better pain relief and other drug benefits.

The present invention has important application in drug abuse applications. When a patient presents in an emergency room as a possible overdose victim, the actual blood levels of the drug and also its identity can be very rapidly assessed by the treating physician using the present invention. This information avoids potentially harmful treatment for overdose by drugs which display the same symptoms as that of the actual overdose substance. Additionally, less draconian detoxification measures can be taken if lower than suspected drug levels are detected using the subject invention. Conversely, toxic levels can be detected even when the patient is not displaying symptoms which would alert the clinician to the actual danger level.

Industrial and Environmental Applications

There are a wide variety of industrial applications for the subject invention. For instance, industrial enzymes can be monitored as to their binding strength, as well as to their presence in a media. Their loss can be monitored in effluent, and their appropriate dispersal can be monitored in feedstock and media.

The invention is very useful in determining optimal conditions for enzyme activity on any particular substrate. Additionally, the enzyme can be easily engineered for optimization, including tailoring for specific uses or working environments. This is done in a manner analogous to designer drug evaluation as explained elsewhere. Thus, tolerance for extreme pH environments, concentrated feedstock, cold and heat, interfering additional materials, and other desirable tolerance can be developed for industrial enzymes and other active materials. The ability of the present inventive films to detect small molecules using TMR's as described in the drug development section above also has excellent use in industrial and environmental applications noteworthy among TMR's to be used for this purpose are the olfactory TMR's. These can bind small odorant molecules and have important applications as an environmental sensor, among others.

The need for chemical sensors to measure analyte concentrations for industrial process control applications, for warning and safety systems, in environmental analysis, etc. is great. Classic chemical analysis such as gas chromatography-mass spectrometry are not conducive to on-site field analysis because of the analytical turn around time, high cost, and the need for technically experienced personnel. The sensor which would be useful in field work analysis therefore requires a material which is chemically sensitive and can specifically bind the analyte in question, and a simple, "user friendly" method to detect when binding of the analyte has occurred. In-line monitoring of public water supplies (eg. swimming pools, drinking water, waste water streams, etc.) for contaminants can be developed.

As shown above, the thin films of chemically functionalized polydiacetylenes of the subject invention act as simple colorimetric biosensors. These films were derivatized with a carbohydrate-based ligand which specifically bound bio-organisms such as viruses. The conjugated polymeric film absorbs in the visible and is initially blue in color. Binding of a virus or other analyte to the derivatized polymer causes a change in color of the film from blue to red. The intensity of the resulting red color corresponds roughly to the quantity of virus.

For more precise quantitative measurement, the film can be scanned with a simple visible absorption spectrometer where the relative change in the intensities at 620 nm (blue) and 550 nm (red) is readily assessed (Table 2). The extent of color response is directly proportional to the concentration of analyte. The present example moves this technology from the realm of bio-diagnostics to the realm of environmental diagnostics by exploring a new class of ligands for which a precedent exists for binding small organic molecules. These ligands are similarly tethered to the polydiacetylene backbone which provides the calorimetric detection.

The inventors couple this calorimetric technology to materials whose chemical properties can be tailored to bind a variety of small organic molecules. Many organic hosts form inclusion complexes with dipolar protic and aprotic compounds. Certain inclusion compounds, or clathrates, such as 1 and 2 (Table 5) have been shown to be highly selective sorbents for organic solvent vapors (Ehlen, et al., *Angew, Chem. Int. Ed. Engl.*, Vol. 32, p. 110, 1993). For example, compound 1 (Table 5) has a pronounced affinity for dioxane and little affinity for butanol, acetone, methanol, 2-propanol, cyclohexane, toluene and water. The lack of affinity to cyclohexane is particularly remarkable given the similarity in chemical structure. Compound 2 (Table 5) on the other hand, shows a pronounced affinity for 1-butanol over the same group of solvents. This breakthrough, combined with the inventors knowledge of calorimetric detection lead to a new class of chemically sensitive materials immobilized on surfaces. Surfaces which have the clathration element, and the detection element both built into a single supra-molecular assembly is a novel method for direct detection of a wide variety of environmental contaminants.

Clathrate forming compounds coupled to polydiacetylene polymer, form a new class of materials which are chemically sensitive, robust, and have unique optical properties. These materials offer a novel, yet simple method of detecting the presence of organic solvents by monitoring the color changes which occur in the film upon binding of the offending compound. No technical expertise is required to use such a detector, thus it is suitable for on-site analysis by persons with little or no technical experience. The molecular level understanding of why clathrate forming compounds of a given structure complex with a given guest molecule leads to a wide variety of clathrate-forming polymeric thin films and may be of further commercial and technological importance.

DETAILED DESCRIPTION OF THE INVENTION

The inventive assay film is a polymerized bilayer assemblage which allows for the direct detection of the presence of a wide range of analytes by changes in spectral criteria. The results can be read by an untrained observer, and the test can be conducted in ambient conditions. Very mild testing conditions are possible, which allows the detection of small biomolecules in a near natural state, providing information as to their interactions and avoiding the risk of modification or degradation of the analyte.

The inventive assay film is composed of the base film, whose surface contains both orienting and detecting head groups. The detecting head groups are composed of a ligand specific to the analyte in question, which is bound to one terminal end of a linear structural linker. This linker, in turn, is bound to the base film by its second terminal end. The base film surface is also provided with lipid ordering head groups.

Figure 1:
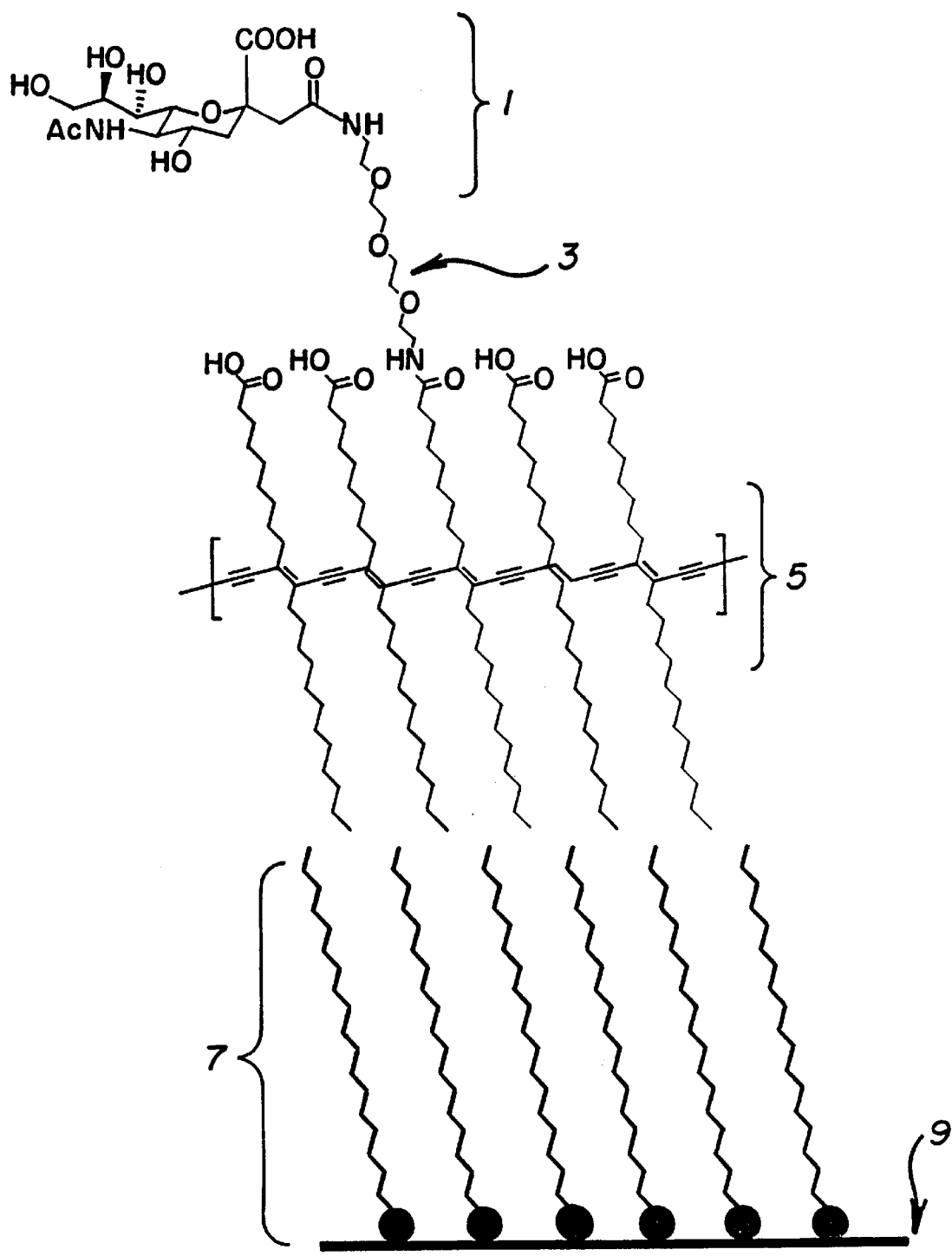
FIG. 1 provides a schematic view of one embodiment of the subject invention.

FIG. 1 provides a schematic depiction of one embodiment of the present invention.

Receptor-binding ligand 1 is shown attached to one terminal end of spacer molecule 3. The second terminal end of spacer molecule 3 is then attached to one of several monomers which have been polymerized into a chromatic detection element 5. A monolayer support layer 7 is provided, in this case on a microscope slide 9. Alternatively, any surface which will accommodate the hydrophobic element 5 can be substituted for the elements 7 and 9. For example, a plastic surface could serve in their place.

Lipid Ordering Groups

The lipids appear to be important in structurally ordering the bilayer so that binding of the analyte produces a detectable color change. Applicants hypothesize that a structuring effect of the ordering groups serves to appropriately stabilize the physical structure of the bilayer to facilitate color stability. In turn, the binding of the analyte to the molecular recognition ligand groups then causes sufficient steric perturbation or stress of the structure to result in a color change. It may be that the stability and relative rigidity engendered by the ordering lipids so unites the bilayer, that a steric change in one area triggers a larger effect in the surface as a whole.

It is not certain which of the many results of binding result in the observed spectral changes. Most likely the changes are due to stresses induced by binding which changes the effective conjugation length of the polymer backbone. The inventive films are highly color sensitive to a number of environmental parameters, such as heat, and these factors may be a component of the observed phenomena as well.

However, the applicants are not bound to any of the above hypothesis which are simply attempts to explain the demonstrated effective assay method of the subject invention.

Materials for use are as head groups in the present invention include $—CH_2OH$, $—CH_2OCONHPh$, $—CH_2OCONHEt$, $—CH_2CH(Et)OCONHPh$, $—(CH_2)_9OH$, $—CH_2OCOPh$, $—CH_2OCONHMe$, $—CH_2OTs$, $—CH(OH)Me$, $—CH_2OCOR_2$, wherein $R_2$ is $n—C_5H_{11}$, $n—C_7H_{15}$, $n—CgH_{19}$, $n—C_{11}H_{23}$, $n—$, $C_{13}H_{27}$, $n—C_{15}H_{31}$, $n—C_{17}H_{35}$ Ph, PhO, or $o—(HO_2C)C_6H_4$, $—OSO_2R_2$, wherein $R_2$ is Ph, $p—MeC_6H_4$, $p—FC_6H_4$, $p—ClC_6H_4$, $p—BrC_6H_4$, $p—MeOC_6H_4$, $m—CF_3C_6H_4$, $2—C_{10}H_7$, or Me $—CO_2^{-M+}$, wherein M is $K^+$, H, $Na^+$ or $Ba^{2+}$.

The preferred materials which can be employed as head groups in the present invention are:

$^{31}CH_2OCONHR_2$ or $—CH_2CONHR_2$ where $R_2$ is Et, n—Bu, $n—C_6H_{13}$, $n—C_8H_{17}$, $n—C_{12}H_{25}$, cyclo-$C_6H_{11}$, Ph, $p—MeC_6H_4$, $m—MeC_6H_4$, $o—ClC_6H_4$, $m—ClC_6H_4$, $p—ClC_6H_4$, $o—MeOC_6H_4$, 3—Thienyl, Me, Et, Ph, $1—C_{10}H_7$, Et, Ph, $EtOCOCH_2$, $BuOCOCH_2$, Me, Et, i—Pr, $n—C_6H_{13}$, $EtOCOCH_2$, $BuOCOCH_2$, Ph, 2,4 $(NO_2)_2C_6H_3OCH_2$, $CH_2CH_2OH$.

The most preferred head groups are taken from $—CH_2COX$, where X is OH, MeO or any salt thereof.

Ligand Group

The ligand group of the present invention can be of a wide variety of materials. The main criteria is that the ligand have an affinity for the analyte of choice. The ligand may be of a broad range, such as when a class of materials is to be assayed. Appropriate ligands include peptides, carbohydrates, nucleic acids or any organic molecules which bind to receptors. For instance, all influenza strains share binding sites to a host receptor molecule. Thus, this molecule can successfully be employed to screen for all influenza strains, including those which have not yet been characterized.

Ligands can also be used in the present invention when they function as competitive binders to the analyte. For instance, a pathogen could be introduced with a test material which is to be tested for the presence of receptor molecule. In absence of this molecule, the pathogen will bind to the assay bilayer and produce a color. To the degree that the pathogen surface is bound to the receptor molecule introduced in the test material, the binding will be diminished. In this way, the presence of receptor molecule can be detected and quantified.

Ligands include, but are not limited to, peptides; carbohydrates; nucleic acids; cell adhesion peptides; transmembrane receptors; hormones; epidermal growth factor for vaccinia analyte; acetylcholine receptor for rabies analyte; complement receptor for Epstein Barr analyte; betaadrenergic receptor for reovirus analyte; ICAM-1 for Rhinovirus analyte; polio virus receptor for polio virus analyte; trisaccharide for cholera toxin analyte; tetrasaccharide for neutorphil analyte; sialic acid and its derivatives and analogs which will bind to coronaviruses, influenza virus, encephalomyelitis, chlamydia, sendi virus, mumps, newcastle disease, myxovirus, encephalo-myocarditis virus, meningitis, and malaria; CD4, sCD4, CD26, vasoactive intestinal peptide, peptide T for HIV analytes, and combinations thereof.

Receptor-Binding Molecules

The use of sialic acid derivatives in one preferred embodiment described in Example 1 below is an example of the use of receptor-binding molecules in this capacity. Receptor-binding molecules are materials on the surface of a host cell to which a pathogen attaches itself as a prelude to the infective event. Selecting these molecules at the ligand group in the present invention has many advantages over other receptor molecules. The recognition site for these molecules tend to be highly genetically conserved in the pathogen because of its obvious criticality to survival. Therefore, different strains of the same pathogen will generally not produce a false negative when such molecules are selected as the ligand group in the subject invention. Also, receptor molecules tend to be smaller and less complex, and often less hydrophobic, than antibodies to the same analyte.

An increasing number of receptor molecules are being recognized, identified, isolated, and synthesized for a large number of pathogens. Many have been improved for use in various analytic and treatment systems. An example of this trend in research is the sialic acid derivative used in the example below of the subject invention. Examples of the receptors for a number of pathogens are provided in the application as Table I. All of these, as well as many more, could be exploited by the method of the subject invention.

Lipid Polymerization Groups

Many different polymerizing groups have been incorporated into lipids and are shown to be effective in monolayer polymerizations. Such moieties include: acetylenes, diacetylenes, alkenes, thiophenes, imides, acrylamides, methacrylates, vinylether, malic anhydride, urethanes, allylamines, siloxanes or vinylpyridinium etc. Lipids containing these groups can be made into homopolymers or mixed polymers. The preferred group for use in this invention is the diacetylene due to its unique optical properties in the polymerized form: polydiacetylene. However, other polymerizing groups could be used when they provide an observable change in properties upon a binding event.

Film Support

The supporting structure on which the film is transferred can be a variety of materials. The material used in certain embodiments of the invention, such as Example 1 below, is a glass slide which has been made hydrophobic by treatment with octadecyltrichlorosilane. Any material which is somewhat hydrophobic such as plastic, mica metal, ceramic or other relatively uniform polymeric surface can be use. Glass is the preferred transferrant support in this invention due to its transparency for ease in reading the color changes. However, non transparent materials can be employed using a reflectance type measurement.

Lipid Tails

The groups comprising the tails of the lipids are of a wide variety. Serving to anchor the polymerized film to the support surface these moieties can be any of the following: $CH_3$—, $CH_3O$—, neo—$C_5H_{11}O$—, cyclo—$C_6H_{11}O$—, $PhCH_2O$—, p—$AcC_6H_4O$—, p—$BzC_6H_4O$—, p—$BrC_6H_4COCH_2O$—, p—$(PhCH{=}CHCO)C_6H_4O$—, p—$(PhCOCH{=}CH)C_6H_4O$—, o—$BzC_6H_4NH$—, p—$BzC_6H_4NH$—, $MeOCH_2CH_2NH$—, n—$C_6H_{13}NH$—, EtO—. The preferred group in this invention is the methyl group.

EXAMPLE 1

Detection of Influenza Virus

The inventive diacetylenic lipid monomers such as compound 1 (FIG. 1) are readily polymerized in monolayers by ultraviolet irradiation to form a conjugated polydiacetylene backbone of alternating eneyne groups using standard art methods (Ticke, et al., *Colloid Polymere Science*, Vol. 255, p. 36, 1977, and Day, et al., *Journal of Polymer Science, Letters to the Editor*, Vol. 16, p. 205, 1978.

In one embodiment of the subject invention, the inventors have developed a polymerized bilayer assembly shown in FIG. 1 composed of a self-assembled monolayer of octadecyltrichlorosilane (OTS) and a LB monolayer of functionalized polydiacetylene.

The inventive LB film was designed to undergo color transition from blue to red solely due to receptor-ligand interactions occurring at the surface of the bilayer. Therefore, the bilayer assembly incorporates both a molecular recognition site and a detection element. This simple color-based sensor enables rapid, qualitative detection of binding by visual inspection of the film or quantitative detection by visible absorption spectroscopy.

The inventive polymerized bilayer assemblies film structure and morphology are shown in FIG. 1 as a film structure and morphology as a schematic diagram of the polymerized bilayer assembly. The siloxane linkages of the bottom monolayer are not shown. FIG. 2 (A) shows an optical micrograph of the sialoside bilayer assembly between crossed polarizers. Large domains up to 150 $\mu$M are visible. Scale: 1 cm=20 $\mu$M.

The inventors initial investigations focused on the binding of the influenza virus to sialic acid as a model system for calorimetric detection. Lipid monomer 2 contains a carbon-linked sialic acid head group that provides a molecular recognition site for the viral lectin, hemagglutinin. FIG. 3 shows matrix lipid 11 sialoside lipid 13 and lactose lipid 15 used in LB film formatting and compounds α- NeuAc 1, β-O-NeuAc 19, and α glucose 21 used for competitive inhibition experiments. The syntheses of compound 13 is reported in Spevak, Journal of *The American Chemistry Society*, Vol. 115, p. 1146, 1993. A carbon glycoside was used instead of the naturally occurring oxygen glycoside to prevent hydrolysis by the neuraminidase, which is also present on the surface of the virus.

The inventors have shown in earlier work that this modification does not alter the binding affinity of hemagglutinin (Spevak, et al., Journal of *The American Chemistry Society*, Vol. 115, p. 1146, 1993). The films were prepared by a modified LB technique in which the carbohydrate head group is presented at the surface of the bilayer. Mixtures of 2% to 5% of glycolipid monomer 13 and matrix lipid monomer 11 were spread on the water surface of a standard LB trough.

The matrix lipid uniformly disperses the sialoside lipid, which allows optimum binding of the virus. The inventors have shown that 1% to 5% of sialoside lipid gives maximum binding of the virus to polymerized liposomes. Ideal mixing of the two components was determined by analysis of the Langmuir isotherms. Various ratios of monomers 11 and 13 give isotherms whose limiting areas and collapse pressures change in direct proportion to the mole fraction of 2 as expected for miscibility. The mixed monolayer was compressed and polymerized on the water surface.

The floating polymerized assembly was lifted by the horizontal touch method onto a glass slide previously coated with a self-assembled monolayer of OTS. The resulting bilayer assembly presents an array of carbohydrate ligands at the surface. The inventors hypothesis that the tetraethylene glycol spacer in sialoside lipid 13 serves to extend the carbohydrate ligand beyond the carboxylic acid head groups of the matrix lipid 11.

Figure 2A:
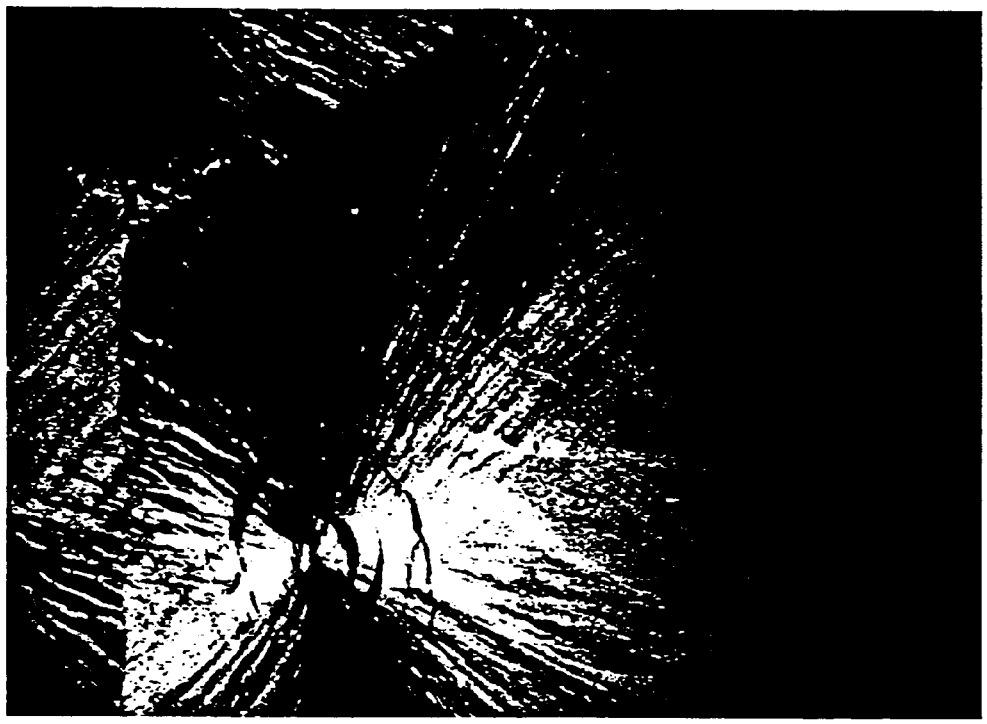
FIGS. 2a and 2b show an optical micrograph of one of the inventive films and the calorimetric response to the influenza virus, respectively.
Figure 2B:
Figures 3A, 3B, 3C, 3D, 3E, 3F:
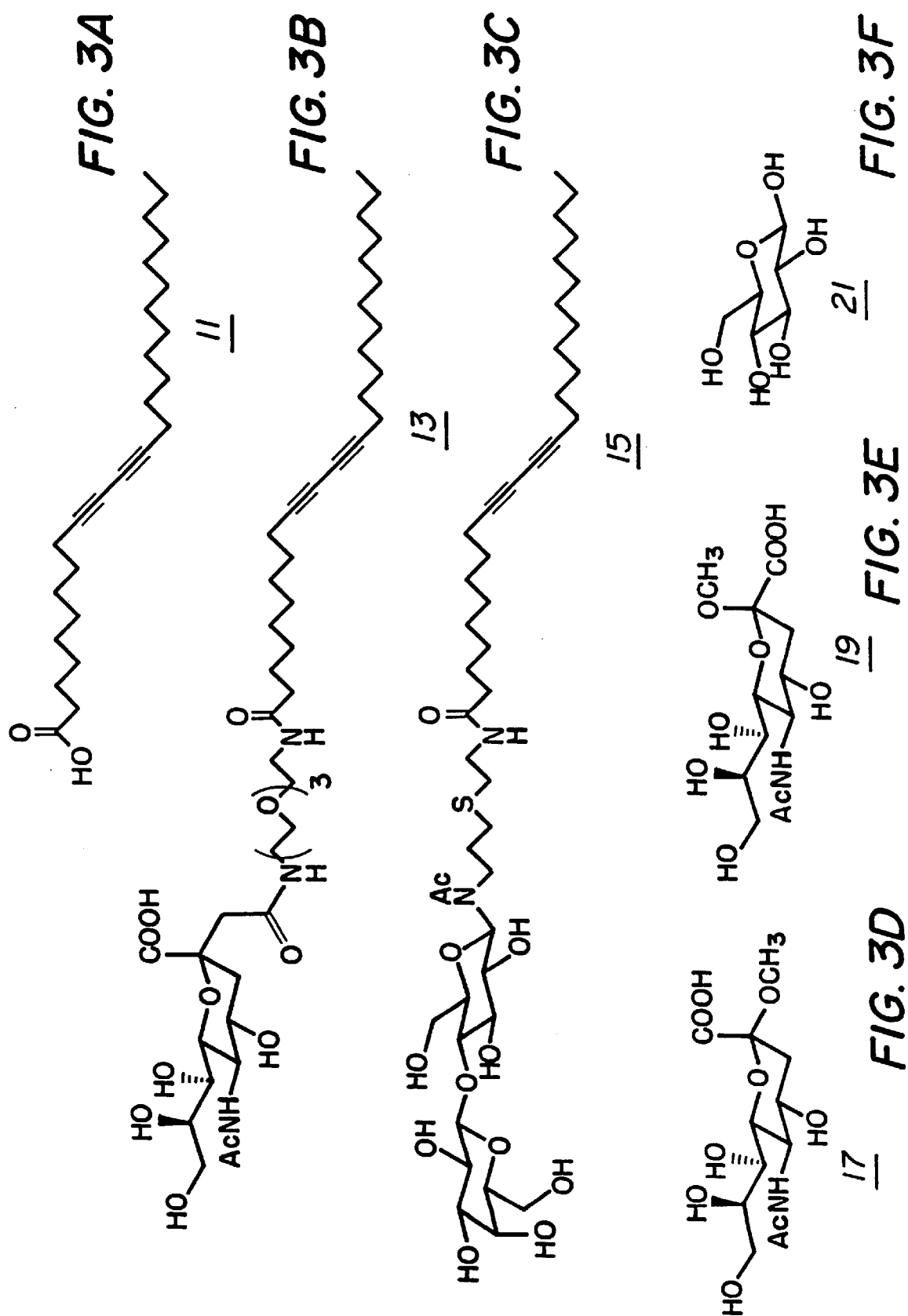
FIGS. 3A–3F show the compounds used in film formation and competitive inhibition experiments. The compounds are matrix lipid (11), sialoside lipid (13), lactose lipid (15), alpha-NeuAc (17), beta-O-NeuAc (19), and alpha-glucose (21); which are FIGS. 3A, 3B, 3C, 3D, 3E, and 3F respectively.
Figure 4:
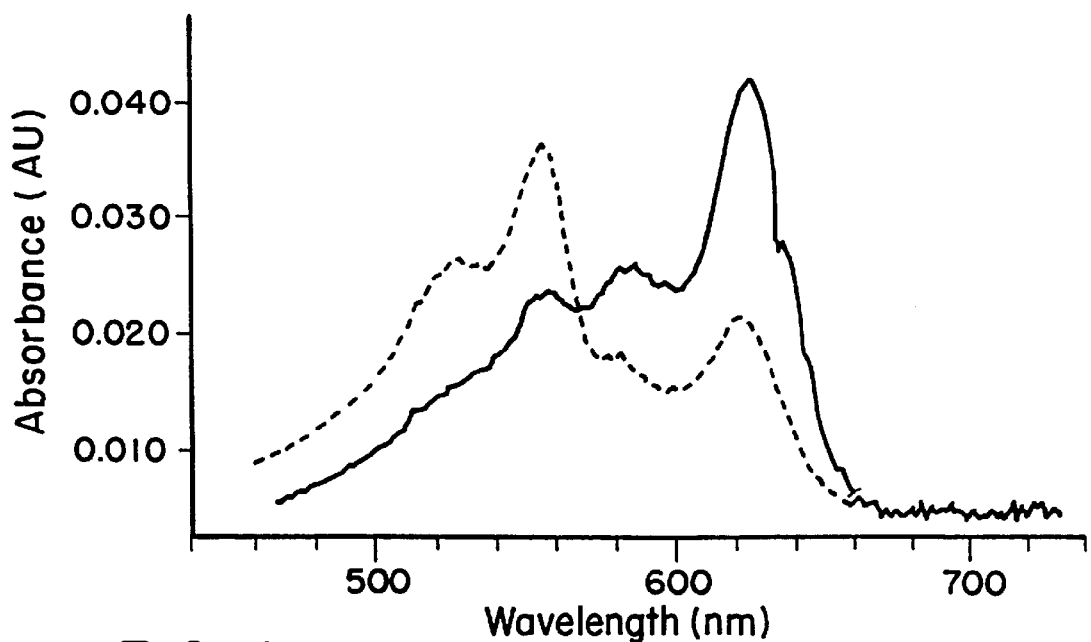
FIG. 4 shows the visible absorption spectrum of a bilayer assembly prior to (solid line) and after (dashed line) viral incubation.
Figure 5:
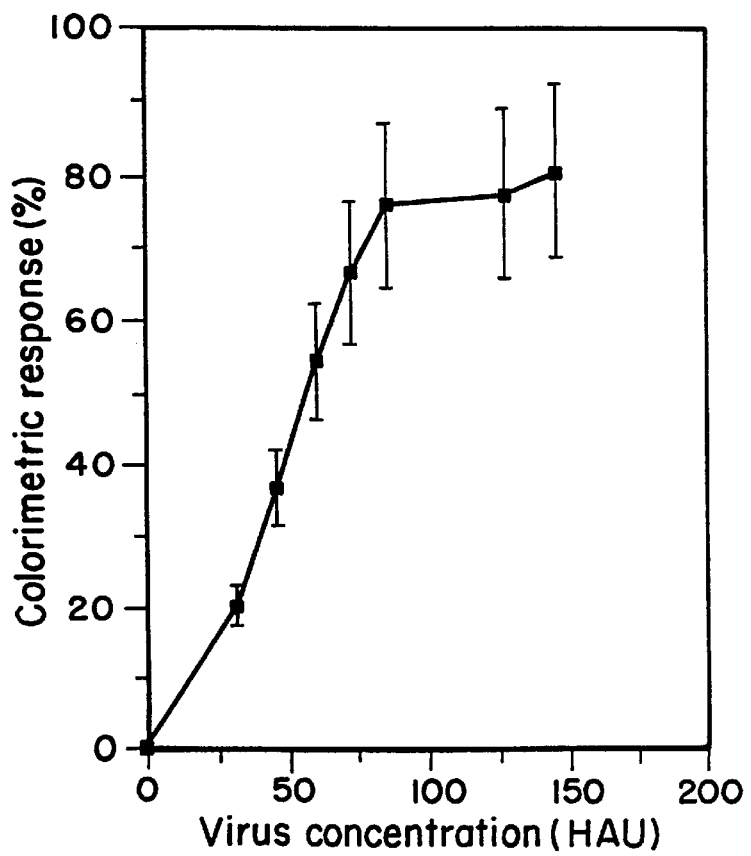
FIG. 5 shows a plot of the colorimetric response of a sialoside bilayer assembly versus successive additions of influenza virus.
Figure 6:
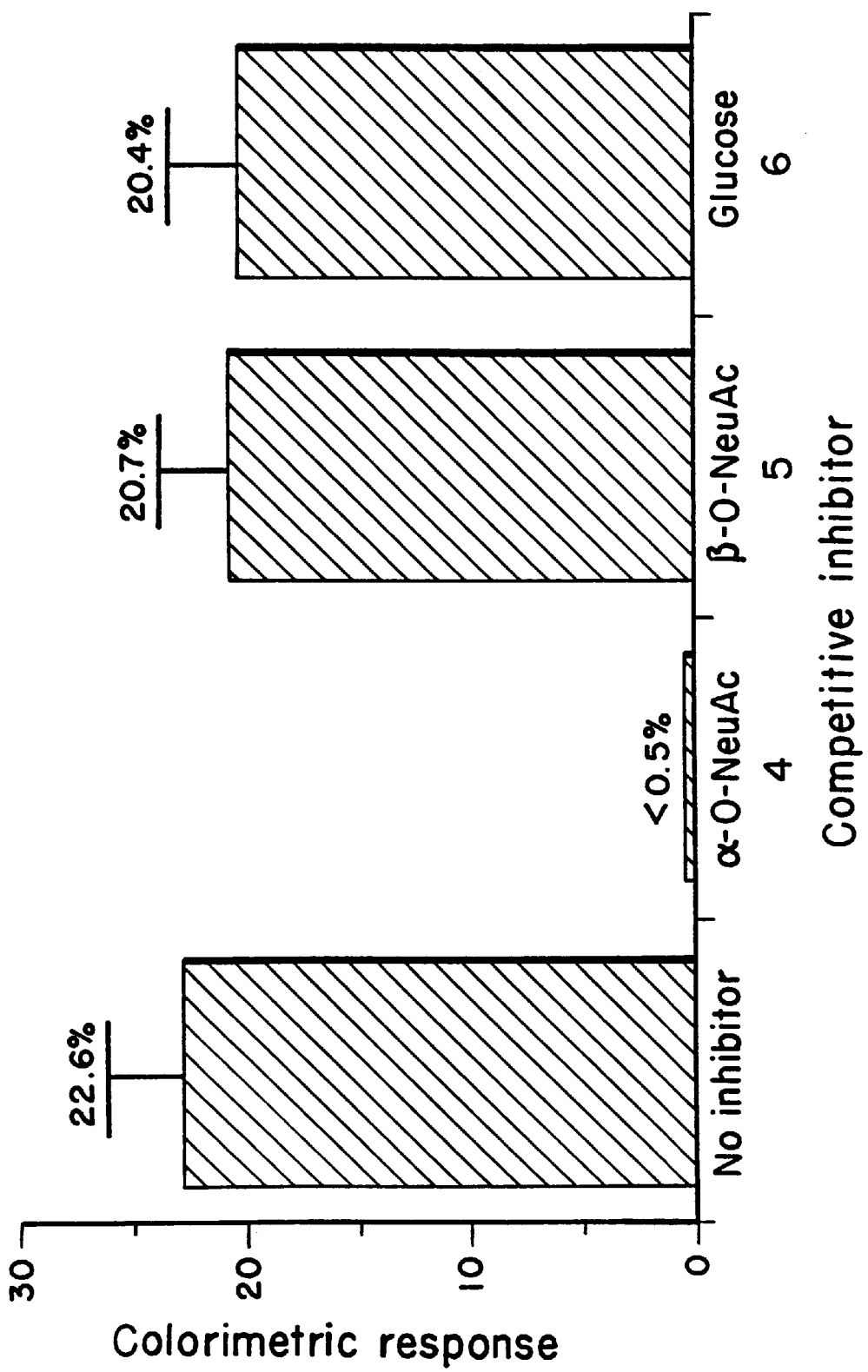
FIG. 6 shows the inhibition of colorimetric response with sialoside bilayers in the presence of viral hemagglutinin with and without inhibitor compounds.

Films prepared in this manner exhibit a high degree of order over a macroscopic range (50 to 150 μM) as evidenced by optical microscopy with the use of crossed polarizers as shown in FIG. 2. The films were further characterized by angle-resolved X-ray photoelectron spectroscopy (XPS) and ellipsometry. The XPS results indicate that the amide nitrogen atoms and the carbonyl carbon atoms of the head groups are localized at the surface relative to the methylene carbons of the lipid chains, demonstrating that the sialoside head group is presented at the surface of the film. Ellipsometric analysis of the polydiacetylene monolayer coated on HF-treated silicon indicates a film thickness of ~40 Å, in agreement with the expected value based on molecular modeling.

The bilayer assembly has a visible absorption maximum of 620 nm and appears as a blue film. When the film is incubated with X31 influenza A virus {PBS (phosphate-buffered saline) buffer, pH 7.4}, the binding of the viral hemagglutinin to the sialic acid residues on the surface results in a blue to red color transition. Table 3 shows the calorimetric response of the film, supported on a glass microscope slide, is readily visible to the naked eye for qualitative evaluation of the presence of virus. The film on the left (blue) has been exposed to a blank solution of PBS. The film on the right (red) has been exposed to 100 HAUs of virus (CR=77%, see text). A calorimetric response of ~15% can be observed visually. No color change is observed when the blue film is incubated with a blank solution of PBS buffer. This result demonstrates a polydiacetylene color transition arising from affinity binding (affinitychromism) rather than thermal annealing (thermochromism).

Previous studies have shown that LB films composed of lipid 1 undergo a blue to red color change when heated at 70° C., which corresponds to the endothermal transition for lipid chain melting. Lipid chain disorder and tangling decrease the effective conjugation length of the polydiacetylene backbone. Similarly, Fourier transform infrared and resonance Raman spectroscopy as well as X-ray data demonstrate that lipid chain packing of the red form of the polymer is different from that of the blue form. Thus, conformational changes in the lipid chains affect the optical properties of the polymer backbone. Binding of the viral hemagglutinin to the sialoside bilayer assembly appears to affect the lipid chain conformations in a manner analogous to thermal annealing.

In addition to qualitative evaluation by visual inspection, the degree of color change is readily quantified by standard visible absorption spectroscopy. The visible absorption spectrum of a bilayer assembly prior to (solid line) and after (dashed line) viral incubation are shown in Table 2. The bilayer assembly was inserted into a quartz cuvette containing PBS buffer (pH 7.4), and the absorption spectrum was obtained. Addition of influenza virus in PBS buffer (pH 7.4) resulted in a chromatic transition following a 30-min. incubation period. Although the film color begins to change within seconds after exposure to virus, 30 min. was found to be the average length of time required for the CR to reach a plateau value in a nonstirred solution. These spectra represent a CR of 50%. The blue-colored film has a strong absorption maximum at 620 nm and a weaker absorption at 550 nm. After incubation with influenza virus, a dramatic change in the visible absorption spectrum occurs. The maximum at 550 nm increases with a concurrent decrease in the maximum at 620 nm, resulting in a red-colored film. In order to quantify the response of a film to a given amount of virus, the visible spectrum of the film before exposure to virus was analyzed as $$B_o = I_{620}/(I_{550} + I_{620})$$

where $B_o$ is defined as the intensity of absorption at 620 nm divided by the sum of the absorption intensities at 550 nm and 620 nm. After exposure to influenza $$B_v = I_{620}/(I_{550} + I_{620})$$

where $B_v$ represents the new ratio of absorption intensities after incubation with the virus. The calorimetric response (CR) of a film is defined as the percent change in B upon exposure to virus $$CR = [(B_o - B_v)/B_o] \cdot 100\%$$

The calorimetric response is directly proportional to the quantity of influenza virus, measured in hemagglutinating units (HAUs), where 1 HAU is defined as the highest dilution of stock virus that completely agglutinates a standard erythrocyte suspension. Table 3 shows a plot of the calorimetric response of a sialoside bilayer assembly versus successive additions of influenza virus. A blue film containing 2% of sialoside lipid 13 and 98% matrix lipid 11 was preincubated in PBS buffer for 30 min., after which successive aliquots of X31 influenza A virus were added. The film was incubated for 30 min. following each addition of virus, and the visible absorption spectrum was recorded. The CR is calculated according to Eq. 3. Linear regression analysis of the first six data points gives a slope of 0.93% ($r^2$=0.985).

Saturation of the colorimetric response occurs at ~80 HAUs. Incubating the red film with a buffer blank (no virus) for 1 hour did not result in a return of the blue color. Thus, the structural changes which result in the color change appear to be irreversible under these conditions.

The specific nature of the interaction between the influenza virus and the sialoside film surface was confirmed by competitive inhibition assays. Table 4 shows that the CR of the film can be inhibited by compounds that bind to viral hemagglutinin. Incubation of a sialoside bilayer assembly with 32 HAUs of influenza virus produces a calorimetric response of 22.6%. However, the same concentration of virus in the presence of 17.3 mM concentration of compound 17 ($K_d$=2 mM) completely suppresses the CR to less than 0.5% due to competitive inhibition. The CR is not diminished in the presence of 17.3 mM concentration of compound 19 ($K_d$>50 mM) or compound 21 that do not compete for binding to viral hemagglutinin. The known inhibitor of influenza hemagglutination, compound 17, has dissociation constant $K_d$ of 2 mM as determined by a standard hemagglutination inhibition assay (HAI).

Incubation of the sialoside bilayer assembly with influenza virus in the presence of the known binding inhibitor 17 results in no CR (CR<0.5%) and the film remains blue. This result demonstrates that the inhibitor effectively competes with the sialoside surface for binding to the virus. When the blue film is exposed to the same quantity of influenza in the presence of a non-inhibitor (compound 19, $K_d$>50 mM, or glucose, compound 21), the color change is identical to a film exposed to influenza alone.

In order to test the capability of the film to predict the value of $K_d$ for an inhibitor, the CR was measured for a series of inhibitor concentrations. The CR increases in a linear fashion ($r^2$=0.995) with decreasing concentrations of inhibitor 17. Extrapolation of this plot to CR=0% gives the inhibitor concentration that completely prevents binding of the virus to the surface. This value represents the minimum inhibitor concentration required to effectively compete with the sialoside surface. The value obtained, 2.5±0.83 mM per 4 HAUs of virus, is in agreement with the value of 2±1.1 mM obtained by a standard HAI assay and 2.8±0.30 mM as obtained by nuclear magnetic resonance spectroscopy.

The inventive inhibition assay described here is direct and easy to perform. This approach avoids the need for red blood cells, which are used in the standard HAI assay. In addition, the subjectivity of reading microtiter plates in the standard HAI assay is replaced by a quantitative spectrophotometric method. This methodology could be applied to screening for new drug candidates or binding ligands.

In order to assess the CR due to nonspecific adhesion, two experiments were performed. In the first experiment, films incorporating lactose lipid 15 were incubated with influenza virus. Lactose is not a ligand for the hemagglutinin lectin. Incubation with 100 HAUs of virus, which is a concentration corresponding to a maximum response in the sialoside films, shows only a small effect (CR of 2 to 4%). In the second experiment, films containing sialoside lipid 13 were exposed to concentrated solutions of bovine serum albumin. Again, the same small CR was observed. These results indicate that nonspecific adsorption of virus or protein to the film surface does not produce the dramatic color change observed from specific receptor-ligand binding.

EXAMPLE 2

Drug Development

A receptor and its reciprocal binding partner (receptor-binding molecule) known to be involved in the physiological regulation of interest are selected. The binding partner is incorporated into the inventive film. In the case of neurotransmission and neurological drug development, for instance, a dopamine receptor can be employed. In the case of drug development toward pathogens such as influenza, for instance, the viruses hemagglutinin receptor can be employed. The binding partner incorporated into the film is dopamine (or a dopamine analog) or sialic acid (or sialic acid analog), respectively. The goal of the drug in the case of hormones and neurotransmitters is to interact with the binding site in a way which effects physiological functions.

If the described receptor is present, it will cause a color change when allowed to bind to the inventive membrane incorporating the binding partner. The receptor can be present in the form of cell membranes from tissues incorporating these receptors.

A candidate drug is then introduced into the system. If the drug binds to the receptor or modifies the binding partner's binding capacity, there is a concomitant decrease in the color change observed in the subject inventive membrane due to competitive inhibition. The ability of the candidate drug to influence binding is quantitated by observing the degree of decrease in signal as compared to the control.

Variations of the above approach are used to suit different systems. In some cases it may be necessary to organize the receptors into large assemblages such as incorporation into polymers, liposomes or membranes. This will amplify the film changes when the receptors bind. However, when a candidate drug is introduced which binds the receptor as above, there is a concomitant decrease in the observed color change.

Another variation that is applicable to this invention requires that the receptor portion be attached to the film. A known receptor is covalently attached to the film at one or more points. This can be accomplished by appending the receptor to the monomer prior to film polymerization (as in the foregoing example for binding partners) or after the film is polymerized through modification of the film's surface. Binding partners then interact with the immobilized receptors distorting the film, giving rise to the color change. In this way, test candidates can be directly screened with receptors giving a positive film response rather than an absence of color change, as in the previous variation.

EXAMPLE 3

Generalized Approach

Generic films can be made where the binding partner can be kept constant and an intermediate linking moiety can be varied to accommodate an ancillary novel binding partner. As an example, a film which has biotin on its surface binds the protein streptavidin. This protein is tetravalent, therefore in its bound state it still has one or more sites available for biotin binding. Novel binding partners need only be derivatized with biotin to attach themselves to the film surface (through the intermediacy of the streptavidin protein). Only a single biotinylated film is prepared, and built up in a sandwich fashion with streptavidin then the biotinylated test binding partner. Exposure of this assembly to the test receptor gives the desired color change. As in the previous example competitive assays are performed to identify new drug candidates.

EXAMPLE 4

Entrapment and Detection of Small Organic Molecules

Table 5

The purpose of this example is to show the development of a new class of functional materials which specifically trap small organic compounds and report the entrapment event by a colorimetric change which can be detected visually. These materials act as simple color-based sensor devices which detect the presence of compounds such as solvents or other toxic pollutants in air or water streams.

The first step involves the synthesis of lipid diacetylene analogs of compounds 1 and 2 a seen in Table 5 by elaborating the secondary methyl group into the lipid tail. The enantiometrically pure ester of PDA (pentacosadiynoic acid) 3 is hydroxylated via molydenum peroxide oxidation to alcohol 4. Diasteriomers are separated and the ester is hydrolyzed to chiral lactate analogs 5 and 6. The ethyl esters are formed and treated with Grignard reagents to give the desired chiral lipid analogs 7 and 8. Variation in the R groups result in a wide variety of new materials in which the specific entrapment capabilities are reviewed.

The monomer-lipid clathrate is ordered and compressed on the water surface using a Langmuir-Blodgett film apparatus. Polymerization of the monolayer by UV irradiation yields the blue colored material as previously described. The material is lifted onto a hydrophobized microscope slide. We test the ability of films of 7 and 8 to entrap dioxane and 1-butanol and to undergo the expected color transition. Because the technique can be generalized, we review derivatives of 1 and 2 and determine how to tune the chemistry to trap a particular small molecule. To date, little is about why the materials 1 and 2 are highly selective to dioxane and 1-butanol, respectively. By examining a series of compounds, we screen a variety of solvents using the calorimetric detection technique to determine which solvent forms the most suitable 'guest' compound. By using computer modeling, cavities are engineered to be the specific size and shape to bind to analyte molecules. We then fully characterize the uncomplexed and complexed film with a variety of standard surface techniques. These include XPS, Auger, Leed, ellipsometry, Raman spectroscopy and STM. All of these enable us to determine the structural requirements of the clathrates in order to rationally design new materials with specific clathration properties.

EXAMPLE 5

Detection of Malaria Merizoites

The inventors have shown that the films containing sialic acid (identical to those described in Example 1) were exposed to erythrocyte containing solutions of malaria merizoites. After overnight exposure to the pathogens the films became pink in color. The color response (CR) in each case was nearly 100%.

We claim:

1. A polymerized bilayer film comprising: a conjugated polymer backbone, linker groups, ligands having direct affinity for an analyte, wherein said ligands are carbohydrates, and ordering head groups, wherein said linker groups are covalently conjugated to said polymer backbone, wherein said ligands are covalently conjugated to said linker groups, wherein said ordering head groups are bound to the surface of said conjugated polymer backbone in positions not occupied by said linker groups, and wherein said polymerized bilayer film undergoes a detectable color change upon binding of said analyte to said ligands.

2. The bilayer film of claim 1, wherein said analyte comprises a pathogen.

3. The bilayer film of claim 2, wherein said pathogen is selected from the group consisting of influenza virus, herpes virus, human immunodeficiency virus, coronavirus, encephalomyelitis, chlamydia, rotavirus, polyomavirus, Streptococcus, Salmonella, sendai virus, mumps virus, Newcastle Disease virus, myxovirus, *E. coli*, encephalomyocarditis virus, and Plasmodium.

4. The bilayer film of claim 1, wherein said conjugated polymer backbone comprises lipid monomers containing chemical moieties selected from the group consisting of diacetylenes, acetylenes, alkenes, thiophenes, pyrroles, vinylpyridinium, and combinations thereof.

5. The bilayer film of claim 1, wherein said ordering head groups are selected from the group consisting of carboxylic acid and salts thereof, esters, hydroxyl groups, amine groups, and amide groups.

6. The bilayer film of claim 1, further comprising a solid support wherein said bilayer film is attached to said solid support.

7. The bilayer film of claim 6, wherein said solid support is selected from the group consisting of plastics, metals, and ceramics.

8. The bilayer film of claim 6, wherein said solid support comprises glass.

9. The bilayer film of claim 8, wherein said glass comprises a hydrophobized glass slide.

10. A polymerized bilayer film comprising: a conjugated polymer backbone, linker groups, ligands having direct affinity for an analyte, wherein said ligands are sialic acid, and ordering head groups, wherein said linker groups are covalently conjugated to said polymer backbone, wherein said ligands are covalently conjugated to said linker groups, wherein said ordering head groups are bound to the surface of said conjugated polymer backbone in positions not occupied by said linker groups, and wherein said polymerized bilayer film undergoes a detectable color change upon binding of said analyte to said ligands.

11. The bilayer film of claim 10, wherein said analyte comprises a pathogen.

12. The bilayer film of claim 11, wherein said pathogen is selected from the group consisting of influenza virus, herpes virus, human immunodeficiency virus, coronavirus, encephalomyelitis, chlamydia, rotavirus, polyomavirus, Streptococcus, Salmonella, sendai virus, mumps virus, Newcastle Disease virus, myxovirus, *E. coli*, encephalomyocarditis virus, and Plasmodium.

13. The bilayer film of claim 10, wherein said conjugated polymer backbone comprises lipid monomers containing chemical moieties selected from the group consisting of diacetylenes, acetylenes, alkenes, thiophenes, pyrroles, vinylpyridinium, and combinations thereof.

14. The bilayer film of claim 10, wherein said ordering head groups are selected from the group consisting of carboxylic acid and salts thereof, esters, hydroxyl groups, amine groups, and amide groups.

15. The bilayer film of claim 10, further comprising a solid support wherein said bilayer film is attached to said solid support.

16. The bilayer film of claim 15, wherein said solid support is selected from the group consisting of plastics, metals, and ceramics.

17. The bilayer film of claim 15, wherein said solid support comprises glass.

18. The bilayer film of claim 17, wherein said glass comprises a hydrophobized glass slide.

19. A polymerized bilayer film comprising: a conjugated polymer backbone, linker groups, ligands having direct affinity for an analyte, wherein said ligands are sialic acid, and ordering head groups, wherein said conjugated polymer backbone comprises a plurality of polymerized diacetylene monomers, wherein said linker groups are covalently conjugated to said diacetylene monomers, wherein said ligands are covalently conjugated to said linker groups, wherein said ordering head groups are bound to the surface of said conjugated polymer backbone in positions not occupied by said linker groups, and wherein said film undergoes a detectable color change upon binding of said analyte to said ligands.

20. The bilayer film of claim 19, wherein said analyte comprises a pathogen.

21. The bilayer film of claim 20, wherein said pathogen is selected from the group consisting of influenza virus, herpes virus, human immunodeficiency virus, coronavirus, encephalomyelitis, chlamydia, rotavirus, polyomavirus, Streptococcus, Salmonella, sendai virus, mumps virus, Newcastle Disease virus, myxovirus, *E. coli*, encephalomyocarditis virus, and Plasmodium.

22. The bilayer film of claim 19, wherein said ordering head groups are selected from the group consisting of carboxylic acid and salts thereof, esters, hydroxyl groups, amine groups, and amide groups.

23. The bilayer film of claim 19, further comprising a solid support selected from the group consisting of plastics, metals, and ceramics, wherein said bilayer film is attached to said solid support.

24. The bilayer film of claim 19, wherein said solid support comprises glass.

25. The bilayer film of claim 24, wherein said glass comprises a hydrophobized glass slide.

26. A polymerized bilayer film comprising: a conjugated polymer backbone, linker groups, sialic acid groups, ordering head groups, and a support structure, wherein said conjugated polymer backbone comprises a plurality of polymerized diacetylene monomers, wherein said linker groups are covalently conjugated to said diacetylene monomers, wherein said sialic acid groups are covalently conjugated to said linker groups, wherein said ordering head groups are bound to the surface of said conjugated polymer backbone in positions not occupied by said linker groups, and wherein said polymerized bilayer film undergoes a detectable color change upon binding of said analyte to said sialic acid groups.

27. A method of making the polymerized bilayer film of claim 1, comprising the steps of:

a) providing:
   i) ligands having direct affinity for an analyte, wherein said ligands are carbohydrates;
   ii) linker groups containing first and second terminal ends;
   iii) lipid monomers;
   iv) lipid monomers comprising ordering head groups; and
   v) a support surface b) attaching said ligands to said lipid monomers, wherein said ligands are attached to said first end of said linker groups and said lipid monomers are attached to said second end of said linker groups to produce monomer-linear structural unit-ligand moieties;

c) mixing said monomer-linear structural unit-ligand moieties with a plurality of said lipid monomers comprising ordering head groups to form a mixture;

d) spreading said mixture of step c) on said support surface to form a bilayer film; and e) polymerizing said bilayer film to form said polymerized bilayer film.

28. The method of claim 27, further comprising the step of transferring said polymerized bilayer film to a solid support.

29. The method of claim 27, wherein after step d), said bilayer film is compressed.

30. The method of claim 27, wherein said support surface is an aqueous surface.

31. A method for the direct detection of an analyte, comprising: contacting the polymerized bilayer film of claim 1 with a sample suspected of containing an analyte; and detecting a color change in said polymerized bilayer film, wherein detection of a color change is indicative of the presence of an analyte.

* * * * *

UNITED STATES PATENT AND TRADEMARK OFFICE
CERTIFICATE OF CORRECTION

Page 1 of 2

PATENT NO. : 6,001,556
DATED : 12/14/99
INVENTOR(S) : Deborah Charych et al.

It is certified that error appears in the above-identified patent and that said Letters Patent is hereby corrected as shown below:

In column 2, line 18, please delete "produce" and insert --produced--.

In column 4, line 43, please delete "*salmonella*" and insert --*Salmonella*--.

In column 4, lines 54 and 63, please delete "calorimetric" and insert --colorimetric--.

In column 12, lines 63 and 64, please delete "calorimetric" and insert --colorimetric--.

In column 13, lines 12 and 37, please delete "calorimetric" and insert --colorimetric--.

In column 14, line 48, please delete "n-CgH$_{19}$" and insert --n-C$_9$H$_{19}$--.

In column 14, line 52, please delete "-CO$_2$-M+" and insert ---CO$_2^-$M$^+$--.

In column 14, line 55, please delete "$^{31}$CH$_2$OCONHR$_2$" and insert -- -CH$_2$OCONHR$_2$--.

In column 14, line 58, please delete "p-CLC$_6$H$_4$" and insert --*p*-ClC$_6$H$_4$--.

In column 16, line 12, please delete "use" and insert --used--.

In column 16, line 63, please delete "calorimetric" and insert --colorimetric--.

In column 17, lines 55 and 60, please delete "calorimetric" and insert --colorimetric--.

In column 18, lines 43, 49 and 54, please delete "calorimetric" and insert --colorimetric--.

In column 19, line 6, please delete "calorimetric" and insert --colorimetric--.

UNITED STATES PATENT AND TRADEMARK OFFICE
CERTIFICATE OF CORRECTION

PATENT NO. : 6,001,556
DATED : 12/14/99
INVENTOR(S) : Deborah Charych et al.

It is certified that error appears in the above-identified patent and that said Letters Patent is hereby corrected as shown below:

In column 21, line 26, between "is" and "about" please insert --known--.
In column 21, line 30, please delete "calorimetric" and insert --colorimetric--.

Signed and Sealed this

Eighth Day of August, 2000

Attest:

Q. TODD DICKINSON

Attesting Officer

Director of Patents and Trademarks